(12) United States Patent
Kim et al.

(10) Patent No.: US 9,305,139 B2
(45) Date of Patent: Apr. 5, 2016

(54) RADIATION TREATMENT PLANNING APPARATUS AND METHOD THEREOF

(71) Applicant: Infinitt Healthcare Co., Ltd., Seoul (KR)

(72) Inventors: Jin Jun Kim, Seoul (KR); Moo Hyun Park, Seoul (KR); Jeong Hoon Han, Seoul (KR)

(73) Assignee: Infinitt Healthcare Co., Ltd., Seoul (KR)

( * ) Notice: Subject to any disclaimer, the term of this patent is extended or adjusted under 35 U.S.C. 154(b) by 0 days.

(21) Appl. No.: 13/936,707

(22) Filed: Jul. 8, 2013

(65) Prior Publication Data

US 2014/0019100 A1   Jan. 16, 2014

(30) Foreign Application Priority Data

Jul. 12, 2012  (KR) .................. 10-2012-0075827

(51) Int. Cl.
   *G06F 19/00* (2011.01)
(52) U.S. Cl.
   CPC ........ *G06F 19/3437* (2013.01); *G06F 19/3481* (2013.01)
(58) Field of Classification Search
   None
   See application file for complete search history.

(56) References Cited

U.S. PATENT DOCUMENTS

| 6,754,374 | B1 * | 6/2004 | Miller et al. ................ 382/128 |
| 7,362,848 | B2 | 4/2008 | Saracen et al. |
| 7,593,505 | B2 | 9/2009 | Saracen et al. |
| 7,995,813 | B2 | 8/2011 | Foshee et al. |
| 8,121,252 | B2 | 2/2012 | Nord et al. |
| 8,666,128 | B2 * | 3/2014 | Chaney et al. ................ 382/128 |
| 8,774,358 | B2 * | 7/2014 | Zankowski ..................... 378/65 |

(Continued)

FOREIGN PATENT DOCUMENTS

| JP | 2006-167117 A | 6/2006 |
| KR | 20090119522 A | 11/2009 |

(Continued)

OTHER PUBLICATIONS

P Bhatnagar, M Subesinghe, C Patel, R Prestwich, and AF Scarsbrook, "Functional Imaging for Radiation Treatment Planning, Response Assessment, and Adaptive Therapy in Head and Neck Cancer," Radiographics. 33(7):1909-29, published 2013, presented as an education exhibit at the 2011 RSNA Annual Meeting.*

(Continued)

*Primary Examiner* — Matthew Bella
*Assistant Examiner* — Soo Shin
(74) *Attorney, Agent, or Firm* — Mintz Levin Cohn Ferris Glovsky and Popeo, P.C.; Kongsik Kim; Colleen H. Witherell (57) ABSTRACT

Disclosed herein is a radiation treatment planning apparatus and method thereof. A radiation treatment planning apparatus comprising: a processor configured to: generate a statistical model for a change in radiation therapy plan (RTP) data based on change data of RTP data collected in association with radiation therapy results data; set first RTP data based on a medical image of a region of interest of a patient; acquire radiation therapy results data based on the first RTP data; acquire statistical data corresponding to the first RTP data and the radiation therapy results data from the statistical model; and generate second RTP data using the statistical data.

13 Claims, 8 Drawing Sheets

(56) References Cited

U.S. PATENT DOCUMENTS

| | | | |
|---|---|---|---|
| 2009/0226060 A1* | 9/2009 | Gering et al. | 382/128 |
| 2011/0267343 A1 | 11/2011 | Foshee et al. | |
| 2012/0123184 A1* | 5/2012 | Otto | A61N 5/1067 600/1 |
| 2013/0085343 A1* | 4/2013 | Toimela et al. | 600/300 |
| 2013/0191146 A1* | 7/2013 | Park et al. | 705/2 |
| 2013/0230224 A1* | 9/2013 | Claude et al. | 382/131 |
| 2013/0274537 A1 | 10/2013 | Park | |

FOREIGN PATENT DOCUMENTS

| | | |
|---|---|---|
| KR | 2010-0119103 A | 11/2010 |
| KR | 20100119106 A | 11/2010 |
| KR | 101090386 B1 | 12/2011 |
| KR | 20120076672 A | 7/2012 |

OTHER PUBLICATIONS

SJ Birkby and SP Harmon, "Reviewing RSNA Education Exhibits for RadioGraphics: The Keystone to Journal Success," RadioGraphics vol. 22, No. 4, 2002, pp. 907-909.*

L. Xing, J. Siebers, and P. Keall, "Computational Challenges for Image-Guided Radiation Therapy: Framework and Current Research," Seminars in Radiation Oncology, Oct. 2007, vol. 17, Issue 4, pp. 245-257.*

* cited by examiner

RADIATION TREATMENT PLANNING APPARATUS AND METHOD THEREOF

CROSS-REFERENCE TO RELATED APPLICATION

This application claims under 35 U.S.C. §119(a) the benefit of Korean Application No. 10-2012-0075827 filed on Jul. 12, 2012, which is incorporated herein by reference.

TECHNICAL FIELD

The present invention relates to RTP (radiation treatment planning or radiation therapy plan) and, more particularly, to an RTP apparatus and method that are capable of establishing a new radiation treatment plan or radiation therapy plan (RTP) using a statistical model for change history of past RTP data and the personalized data of a patient upon establishing a subsequent RTP.

BACKGROUND ART

Generally, in hospitals, many systems or apparatuses should be used to perform radiation treatment. These systems and apparatuses include an electronic medical record (EMR) system, an order communication system (OCS), a picture archiving and communication system (PACS), an RTP system, and a radiation treatment apparatus (for example, a linear accelerator (LINAC)).

The OCS is a system that transfers a database (DB) in which a variety of types of medical information and patients' medical examination data are stored and prescriptions which are written when doctors examine patients to individual corresponding treatment departments over a communication network.

The EMR system is a system that is configured for the purposes of the storage and searching of electronic medical records.

The PACS is a system that can store images captured by at least one of medical imaging apparatuses, including a Computed Tomography (CT) scanner, a Magnetic Resonance Imaging (MRI) scanner, a Positron Emission Tomography (PET) scanner, a CT simulator, and a Computed Radiography (CR) system, in the form of computer files and transfer them, and is equipment that has been introduced into most middle-scale hospitals.

The RTP system is a system for establishing (drawing up) a radiation treatment plan for a patient using a program, and is configured to establish a radiation treatment plan, that is, it draws up radiation treatment plan information and calculates and reviews radiation doses. Using such an RTP system, a user may select an optimal image from among images of a cancer region of a patient acquired by a CT scanner or an MRI scanner, or may view a medical image of the patient, directly convert the image into a digital image, perform basic image processing on the digital image, set reference coordinates for the acquired image, perform contouring on each region, and calculate the direction and dose of a radiation beam based on the size of cancer tissue.

The fundamental principle of radiation treatment is intended to minimize not only acute and chronic radioactive reactions or complications, which may occur in normal tissue, but also the occurrence of a secondary tumor while increasing the effects of cancer treatment. For this purpose, there is a need to establish an appropriate radiation treatment plan.

The radiation treatment apparatus is an apparatus that actually performs radiation treatment on a patient according to an RTP that is drawn up by the RTP system.

The tumor treatment methods of radiation oncology have been newly developed and diversified, and accordingly treatment apparatuses and applications for the various treatment methods have been newly developed.

In the field of radiation oncology, the process of radiation treatment that is performed on a patient is as follows. First, in order to obtain information about the tumor of a patient, medical images of the patient are acquired via a medical imaging apparatus. Thereafter, an RTP is made based on the medical images of the patient via an RTP system. Thereafter, radiation treatment is performed using a radiation treatment apparatus based on the RTP that has been made via the RTP system.

In this case, a LINAC, a Brachytherapy system, a Cyberknife, and a tomotherapy system have been developed and used as radiation treatment apparatuses, and these radiation treatment apparatuses are appropriately selected and used depending on the state of the tumor of a patient and the region of treatment.

An RTP system according to the technology of a conventional embodiment establishes radiation treatment plans (RTPs) using only medical images of patients. That is, since the conventional RTP system does not take into account singularities different for respective patients, such as states and ages of patients, the same RTP may be established and then radiation treatment may be performed based on the same RTP, even in the case in which the corresponding patient has singularities.

Accordingly, there arises a need for an apparatus for establishing RTPs using information about the personal singularities of patients as well as medical images.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

Accordingly, the present invention has been made keeping in mind the above problems occurring in the prior art, and an object of the present invention is to provide an RTP apparatus and method, which establish a new RTP using a statistical model for the change history of past RTP data and the personalized data of a patient, thus reducing the time and cost required to establish RTPs.

In detail, the present invention is intended to provide an RTP apparatus and method, which establish a new RTP in consideration of a statistical model generated based on change data of RTP data collected in association radiation treatment results data or a statistical model generated based on change data of RTP data collected in association with the results of a comparison between medical images, and the personalized data of a patient, thus generating RTP data that considers the singularities of each individual patient, and reducing the time and cost required to establish an RTP.

Another object of the present invention is to provide an RTP apparatus and method, which can establish new RTP data using a statistical model for the change history of past RTP data and a radiation treatment purpose.

In order to accomplish the above objects, a radiation treatment planning (RTP) apparatus according to an embodiment of the present invention includes a statistical model generation unit for generating a statistical model for a change in radiation treatment plan (RTP) data based on change data of RTP data collected in association with radiation treatment results data; a treatment plan setting unit for setting first RTP data based on a medical image of a region of interest of a patient; a treatment result acquisition unit for acquiring radiation treatment results data based on the set first RTP data; a statistical data acquisition unit for acquiring statistical data corresponding to the acquired first RTP data and the radiation treatment results data from the statistical model; and a treatment plan generation unit for generating second RTP data using the acquired statistical data.

The treatment plan generation unit may generate the second RTP data using the statistical data and personalized data of the patient, and the personalized data may include at least one of age, gender, weight, height, medical history, occurrence of menopause, diagnosis, an Eastern Cooperative Oncology Group (ECOG)/Karnofsky Performance Status (KPS) index, occurrence of metastasis, primary Tumor, regional lymph Node, distant Metastasis (TNM) class, chemical therapy, a region of treatment, a treatment pattern, immunity, sensitivity, and singularities of past treatment.

The treatment plan generation unit may generate the second RTP data using the statistical data and a treatment purpose of RTP data to be generated.

The treatment plan setting unit may set first RTP data corresponding to the medical image among a plurality of preset RTP data, and may further set the first RTP data among the plurality of RTP data using the medical image and personalized data of the patient.

The RTP apparatus of the present invention may further include a determination unit for providing the generated second RTP data to a user, and determining whether to use the second RTP data as RTP data of the patient depending on input of the user.

A radiation treatment planning (RTP) apparatus according to another embodiment of the present invention may include a statistical model generation unit for generating a statistical model for a change in radiation treatment plan (RTP) data based on change data of RTP data collected in association with results of a comparison between medical images; a treatment plan setting unit for setting first RTP data based on a first medical image of a region of interest of a patient; a medical image comparison unit for comparing a second medical image acquired from the region of interest with the first medical image; a statistical data acquisition unit for acquiring statistical data corresponding to the results of the comparison between the first medical image and the second medical image and the first RTP data from the statistical model; and a treatment plan generation unit for generating second RTP data using the acquired statistical data.

A radiation treatment planning (RTP) system according to an embodiment of the present invention includes a server for generating a statistical model for a change in radiation treatment plan (RTP) data based on change data of RTP data collected in association with radiation treatment results data, and storing radiation treatment results data and personalized data for each patient; a treatment plan setting unit for setting first RTP data based on a medical image of a region of interest of a target patient; a data acquisition unit for requesting and receiving radiation treatment results data for the region of interest of the target patient based on the first RTP data and personalized data of the target patient from the server; a statistical data acquisition unit for acquiring statistical data corresponding to the set first RTP data and the radiation treatment results data from the statistical model generated by the server; and a treatment plan generation unit for generating second RTP data using the acquired statistical data.

A radiation treatment planning (RTP) method according to an embodiment of the present invention includes generating, by a processor, a statistical model for a change in radiation treatment plan (RTP) data based on change data of RTP data collected in association with radiation treatment results data; setting, by the processor, first RTP data based on a medical image of a region of interest of a patient; acquiring, by the processor, radiation treatment results data based on the set first RTP data; acquiring, by the processor, statistical data corresponding to the acquired first RTP data and the radiation treatment results data from the statistical model; and generating, by the processor, second RTP data using the acquired statistical data.

A radiation treatment planning (RTP) method according to another embodiment of the present invention includes generating, by a processor, a statistical model for a change in radiation treatment plan (RTP) data based on change data of RTP data collected in association with results of a comparison between medical images; setting, by the processor, first RTP data based on a first medical image of a region of interest of a patient; comparing, by the processor, a second medical image acquired from the region of interest with the first medical image; acquiring, by the processor, statistical data corresponding to the results of the comparison between the first medical image and the second medical image and the first RTP data from the statistical model; and generating, by the processor, second RTP data using the acquired statistical data.

DETAILED DESCRIPTION OF THE DISCLOSURE

The above and other objects and features of the present invention will be more clearly understood from the following detailed description taken with reference to the accompanying drawings.

The terms used herein are used merely to describe specific embodiments, but are not intended to limit the present invention. The singular expressions include plural expressions unless explicitly stated otherwise in the context thereof. It should be appreciated that in this application, the terms "include(s)," "comprise(s)", "including" and "comprising" are intended to denote the presence of the characteristics, numbers, steps, operations, elements, or components described herein, or combinations thereof, but do not exclude the probability of presence or addition of one or more other characteristics, numbers, steps, operations, elements, components, or combinations thereof.

Unless defined otherwise, all terms used herein, including technical terms or scientific terms, have the same meanings as those generally understood by persons of ordinary skill in the technical field to which the present invention pertains. The terms, such as terms that are generally used and defined in dictionaries, should be construed as having meanings identical to those that are used in the context of related technology, and should not be construed as having ideal or excessively formal meanings unless explicitly defined otherwise.

Preferred embodiments of the present invention will be described in detail with reference to the accompanying drawings. In the following description of the present invention, if it is determined that detailed descriptions of related well-known configurations or functions may make the gist of the present invention obvious, the detailed descriptions will be omitted.

However, the present invention is not restricted or limited to the embodiments. The same reference symbols represented throughout the drawings designate the same elements.

Hereinafter, a radiation treatment planning (RTP) apparatus and method according to embodiments of the present invention will be described in detail with reference to FIGS. 1 to 8.

Figure 1:
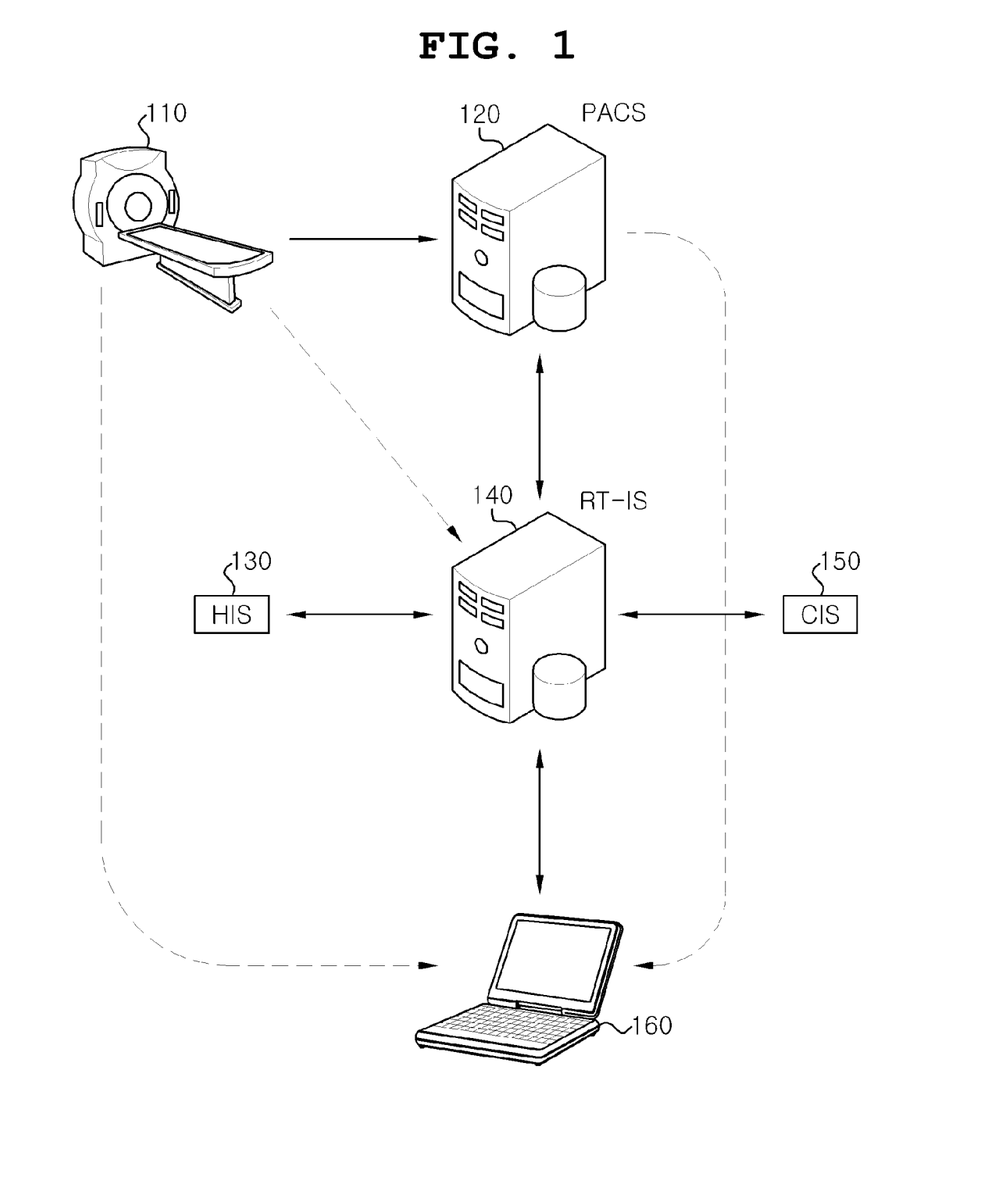
FIG. 1 shows a system of an embodiment illustrating an RTP apparatus according to the present invention.

FIG. 1 shows a system of an embodiment illustrating an RTP apparatus according to the present invention.

Referring to FIG. 1, the system includes a medical imaging device 110, a picture archiving and communication system (PACS) 120, a hospital information system (HIS) 130, a radiation treatment information management server (RT-IS) 140, a clinical information system (CIS) 150, and a client device 160.

The medical imaging device 110 is a device for acquiring medical images of a patient, and is configured to capture medical images of the patient, to convert the captured medical images into a Digital Imaging and Communications in Medicine (DICOM) format or a non-DICOM format, and to transfer resulting medical images to at least one of the PACS 120, the RT-IS 140, and the client device 160.

In this case, the medical imaging device 110 may include a Computed Tomography (CT) scanner, a Magnetic Resonance Imaging (MRI) scanner, a Positron Emission Tomography (PET) scanner, a CT simulator, and a Computed Radiography (CR) system.

The PACS 120 stores the medical images received from the medical imaging device 110 in a DICOM format, and transfers the stored medical images to a device or a system which requests the medical images.

In this case, the PACS 120 may transfer the medical images to at least one of the RT-IS 140 and the client device 160.

The HIS 130 is a system for computerizing and automating the overall management tasks of a hospital, and is configured to manage and transfer all data occurring within the hospital in connection with the registration of patients to medical treatment and accounting, and efficiently manage all administration tasks of the hospital.

Here, the HIS 130 may manage and transfer data in conjunction with an OCS, an EMR system, etc.

The CIS 150 is a digital clinical system for proving assistance to store biometric signals and data generated from electrocardiogram (ECG) equipment and typical clinical equipment in a digital format, and to enable the signals and data to be retrieved and examined over a network.

The RT-IS 140 is a server for storing and managing radiation treatment (RT)-related information and is configured to store medical images of a patient, previous RTP data of the patient, radiation treatment results data (or radiation therapy results data) based on the RTP data, a statistical model based on the radiation treatment results data, the personalized data of the patient, etc., which are required to generate RTP data.

In this case, the RT-IS 140 may collect/store the personalized data of the patient in conjunction with the HIS 130, the CIS 150, etc., and may store a plurality of preset RTP data. The statistical model may be a statistical model for a change in RTP data generated based on the change data of a plurality of RTP data collected in association with radiation treatment results data. Such a statistical model may be generated by the RT-IS 140 or may be generated by separate equipment and stored in the RT-IS 140.

Here, the plurality of preset RTP data may be reference RTP data previously modeled in conformity with specific criteria, and the personalized data of the patient may include at least one of age, gender, weight, height, medical history, occurrence of menopause, diagnosis, an Eastern Cooperative Oncology Group (ECOG)/Karnofsky Performance Status (KPS) index, occurrence of metastasis, TNM class, chemical therapy, a region of treatment, a treatment pattern, immunity, sensitivity, and the singularities of past treatment. The KPS index is one of methods of classifying the whole body activities of the patient, and denotes an index representing physical status from death to normal body status by a value ranging from 0 to 100[%]. Of course, the KPS index is not necessarily limited to data in which personalized data is described, and may include all information about the characteristics of each individual patient.

Furthermore, the RT-IS 140 may perform the function of the RTP apparatus according to the present invention, and this will be described in detail later with reference to FIGS. 2 to 4.

Furthermore, the RT-IS 140 may store not only a statistical model associated with the radiation treatment results data, but also a statistical model associated with the results of a comparison between medical images.

In this case, the RT-IS 140 may generate a statistical model based on the change history of collected RTP data associated with the radiation treatment results data of a plurality of patients or the results of a comparison between medical images, and the statistical model may be composed of statistical data respectively corresponding to specific conditions, for example, RTP data, radiation treatment results data, etc.

The client device 160, which is a user device for establishing an RTP, may be an RT-PACS, and may be provided with the medical images of a patient from at least one of the medical imaging device 110, the PACS 120, and the RT-IS 140, may be provided with radiation treatment results data based on the RTP data of the patient and the personalized data of the patient from the RT-IS 140, and may also be provided with statistical data corresponding to a specific condition from the statistical model. Of course, the client device 160 may also directly store the personalized data of the patient and the statistical model depending on the circumstances.

Further, the client device 160 is a device corresponding to the RTP apparatus of the present invention, and may establish an RTP therein or may establish an RTP in conjunction with the RT-IS 140.

Such an RTP apparatus according to the present invention will be described in detail with reference to FIGS. 2 to 4.

Figure 2:
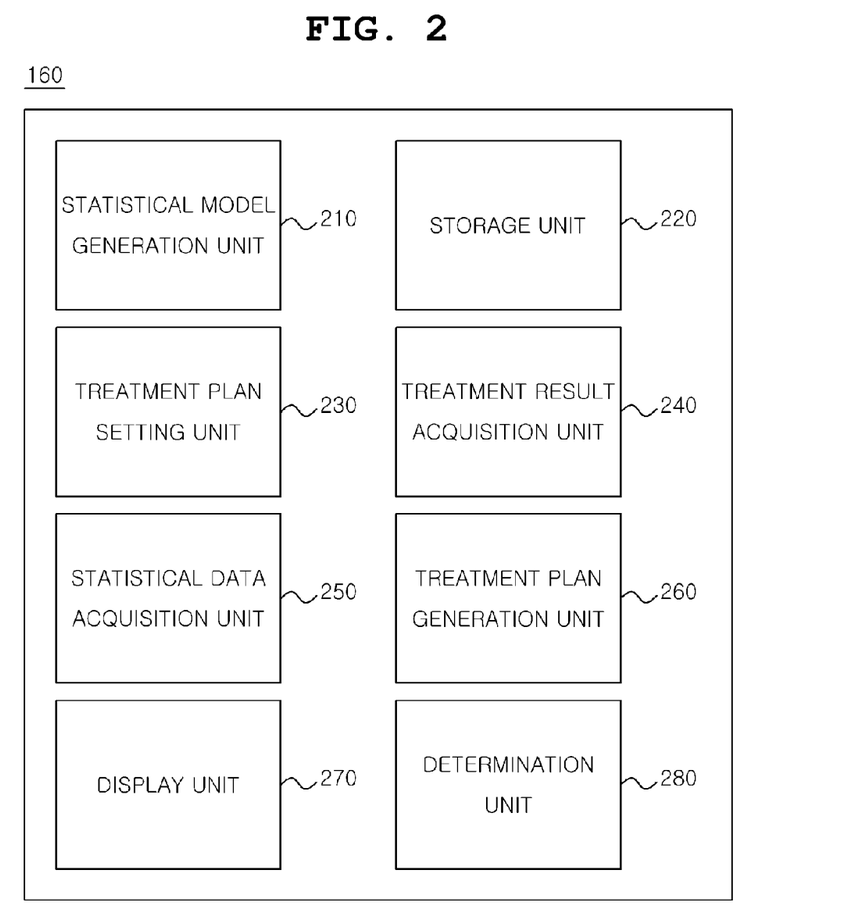
FIG. 2 shows the configuration of an RTP apparatus according to an embodiment of the present invention.

FIG. 2 illustrates the configuration of an RTP apparatus according to an embodiment of the present invention, wherein the RTP apparatus may be implemented in the RT-IS 140 or the client device 160, but, in FIG. 2, the client device 160 will be described as an example.

Referring to FIG. 2, the RTP apparatus 160 includes a statistical model generation unit 210, a storage unit 220, a treatment plan setting unit 230, a treatment result acquisition unit 240, a statistical data acquisition unit 250, a treatment plan generation unit 260, a display unit 270, and a determination unit 280.

The statistical model generation unit 210 generates a statistical model for a change in RTP data based on the change data of RTP data collected in association with radiation treatment results data.

In this case, the statistical model generation unit 210 may extract a kind of transformation formula, a transformation condition, a coefficient, etc. based on details of the RTP data that were corrected in the past depending on the radiation treatment results data using a neural net, a linear regression method, etc., and may generate a statistical model based on them.

The storage unit 220 may store medical images of patients, a plurality of preset RTP data, that is, modeled reference RTP data, previous RTP data of the patients, radiation treatment results data based on the previous RTP data of the patients, the statistical model generated by the statistical model generation unit 210, and the personalized data of the patients.

Here, personalized data may include at least one of age, gender, weight, height, medical history, occurrence of menopause, diagnosis, an ECOG/KPS index, occurrence of metastasis, TNM class, chemical therapy, a region of treatment, a treatment pattern, immunity, sensitivity, and the singularities of past treatment, and such personalized data may be directly acquired from EMR, HIS or the like, and may be acquired from an RT-IS.

Of course, the personalized data is not limited to the above-described items and may additionally include a reaction to radiation, other types of physical information such as the thickness of an arm, a change in weight after past radiation treatment has been performed, etc.

Furthermore, the storage unit 220 may include at least one preset RTP data for the radiation treatment of each patient. Here, the at least one preset RTP data may be any one of modeled reference RTP data or may be RTP data newly generated using the reference RTP data.

The treatment plan setting unit 230 sets the RTP data of the patient based on a medical image of a region of interest of the patient, that is, the radiation treatment region of the patient.

In this case, the treatment plan setting unit 230 may set the RTP data of the patient in response to the input of a user, that is, a radiation treatment specialist, and may also set RTP data corresponding to the medical image of the patient among a plurality of preset RTP data. Of course, if necessary, the treatment plan setting unit 230 may set the corresponding RTP data among a plurality of preset RTP data by additionally using the personalized data of the patient.

Here, the treatment plan setting unit 230 may extract information about a region of radiation treatment, the size of cancer, etc. from the medical image of the patient, and may set RTP data corresponding to the extracted information.

Figure 3:
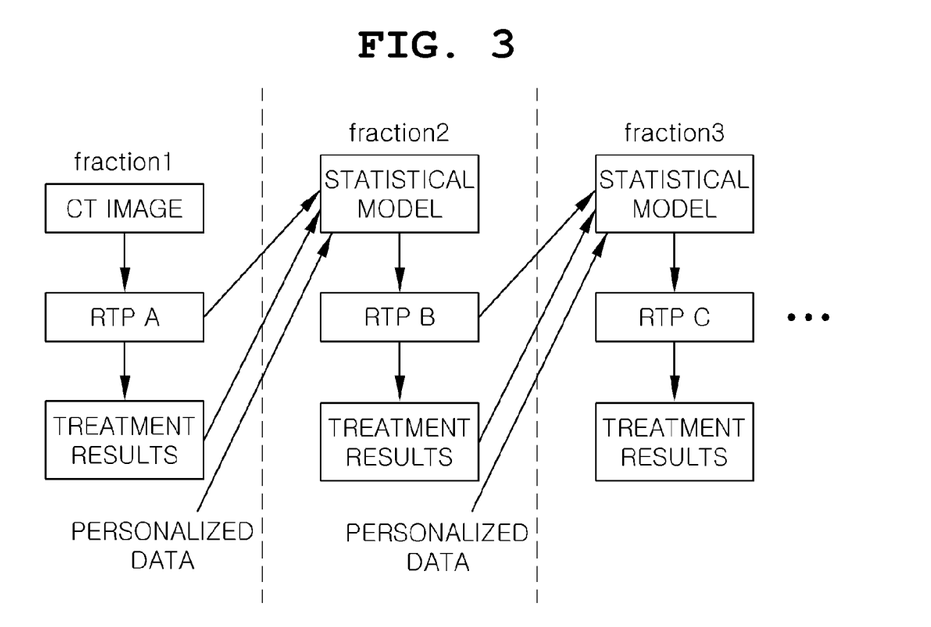
FIG. 3 shows an illustrative diagram illustrating the RTP apparatus shown in FIG. 2.

For example, as in the case of fraction 1 shown in FIG. 3, RTP A corresponding to a CT image of a patient is set using the CT image of the patient in fraction 1.

The treatment result acquisition unit 240 acquires radiation treatment results data based on the RTP data acquired by the treatment plan setting unit 230.

In this case, the radiation treatment results data may include not only historical information, such as a dose volume histogram (DVH) and radiation doses to a tumor and normal internal organs, but also numerical data, such as the power consumption (monitor unit: MU) of a radiation treatment apparatus.

The statistical data acquisition unit 250 acquires statistical data corresponding to the set RTP data of the patient and radiation treatment results data from the statistical model.

For example, as in the case of fraction 2 shown in FIG. 3, statistical data corresponding to RTP A in fraction 1 and treatment results based on RTP A is acquired from the statistical model.

The treatment plan generation unit 260 generates subsequent RTP data for the region of interest of the patient using the statistical data acquired by the statistical data acquisition unit 250 and the personalized data of the patient.

In this case, the treatment plan generation unit 260 may generate subsequent RTP data of the patient by additionally considering the treatment purpose of RTP data.

For example, as shown in FIG. 3, RTP B is generated using the statistical data acquired from the statistical model and the personalized data of the patient in fraction 2, statistical data corresponding to RTP B and treatment results in fraction 2 is acquired from the statistical model in fraction 3, and RTP C is generated using the acquired statistical data and the personalized data of the patient.

As another embodiment, the treatment plan generation unit 260 may generate RTP data in the corresponding fraction using a radiation treatment purpose and statistical data acquired from the statistical model in the fraction, and even the personalized data of the patient if necessary. Of course, the statistical data acquired from the statistical model is the statistical data of the statistical model corresponding to RTP data and treatment results in the previous fraction.

Here, the treatment purpose may be determined in fractions, but may be determined in plans, each including a plurality of fractions, wherein it is preferable to determine a treatment purpose for each plan.

In this case, the treatment purpose may include a purpose to completely eliminate a tumor, a purpose to mitigate pain, a purpose to reduce a tumor, a purpose to prevent recurrence, etc., and may be a factor for determining the direction of a subsequent plan by selecting only one from among a plurality of purposes, such as checking whether a patient is male or female.

The display unit 270 displays the RTP data generated by the treatment plan generation unit 260 on a screen, thus providing newly generated RTP data to the user.

In this case, the display unit 270 may be provided in the client device 160, but may not be provided in the RT-IS 140.

The determination unit 280 may receive user input, that is, input related to whether to use generated RTP data, from the user and determine whether to use the generated RTP data as the RTP data of the patient according to the received user input.

In this case, the determination unit 280 may be provided in the client device 160, but may not be provided in the RT-IS 140.

FIGS. 2 and 3 illustrate the generation of RTP data between fractions, wherein an RTP apparatus according to the present invention is not limited by the generation of RTP data between fractions and may generate new RTP data in a single fraction. This procedure will be described with reference to FIGS. 4 and 5.

Figure 4:
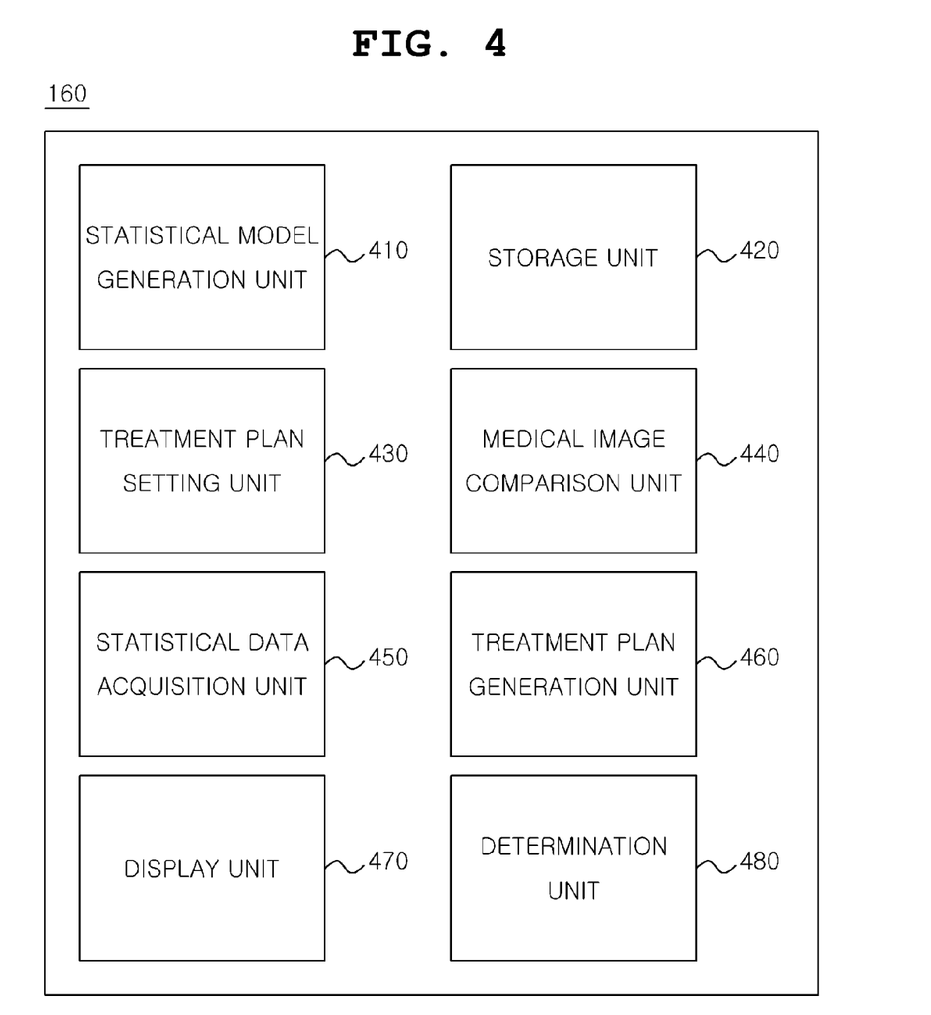
FIG. 4 shows the configuration of an RTP apparatus according to another embodiment of the present invention.

FIG. 4 is a diagram showing the configuration of an RTP apparatus according to another embodiment of the present invention, wherein the RTP apparatus may be implemented in an RT-IS or a client device, but, in FIG. 4, the client device will be described as an example.

Referring to FIG. 4, the RTP apparatus 160 includes a statistical model generation unit 410, a storage unit 420, a treatment plan setting unit 430, a medical image comparison unit 440, a statistical data acquisition unit 450, a treatment plan generation unit 460, a display unit 470, and a determination unit 480.

The statistical model generation unit 410 generates a statistical model for a change in RTP data based on the change data of RTP data collected in association with the results of a comparison between medical images.

In this case, the statistical model generation unit 410 may extract a kind of transformation formula, a transformation condition, a coefficient, etc. based on details of the RTP data that were corrected in the past depending on the radiation treatment results data using a neural net, a linear regression method, etc., and may generate a statistical model based on them.

The storage unit 420 may store medical images of patients, a plurality of preset RTP data, that is, modeled reference RTP data, the previous RTP data of the patients, the personalized data of the patients, and the statistical model generated by the statistical model generation unit 410.

Here, personalized data may include at least one of age, gender, weight, height, medical history, occurrence of menopause, diagnosis, an ECOG/KPS index, occurrence of metastasis, TNM class, chemical therapy, a region of treatment, a treatment pattern, immunity, sensitivity, and the singularities of past treatment, and such personalized data may be directly acquired from EMR, HIS or the like, may be acquired from an RT-IS, or may also be previously stored in the server.

The treatment plan setting unit 430 sets the RTP data of the patient based on a medical image of a region of interest of the patient, that is, the radiation treatment region of the patient.

In this case, the treatment plan setting unit 430 may set the RTP data of the patient in response to the input of a user, that is, a radiation treatment specialist, and may also set RTP data corresponding to the medical image of the patient among a plurality of preset RTP data. Of course, if necessary, the treatment plan setting unit 430 may set the corresponding RTP data among a plurality of preset RTP data by additionally using the personalized data of the patient.

Here, the treatment plan setting unit 430 may extract information about a region of radiation treatment, the size of cancer, etc. from the medical image of the patient, and may set RTP data corresponding to the extracted information.

Figure 5:
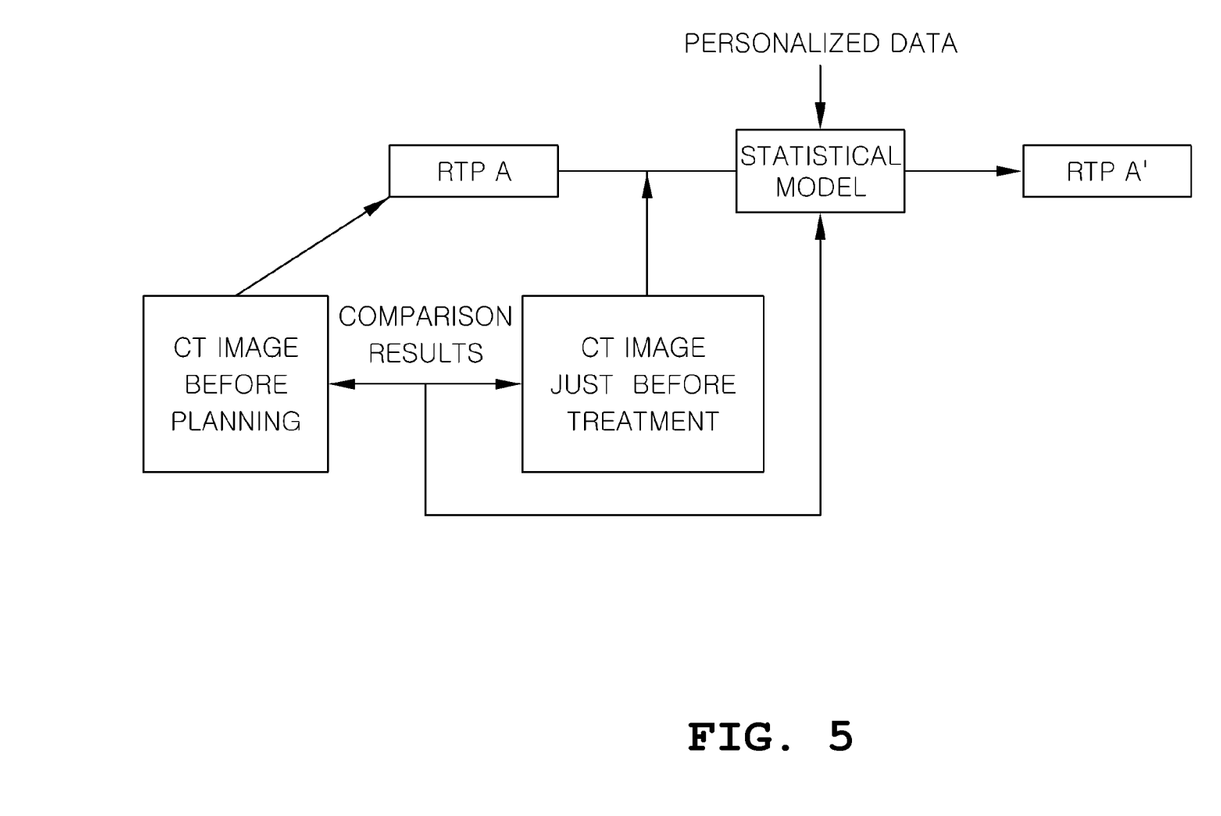
FIG. 5 shows an illustrative diagram illustrating the RTP apparatus shown in FIG. 4.

For example, as shown in FIG. 5, RTP A which is RTP data is set using a CT image before planning.

The medical image comparison unit 440 compares a medical image of a patient required to acquire RTP data with a medical image of the patient after the RTP data has been acquired.

For example, as shown in FIG. 5, a CT image before the RTP data is set is compared with a CT image after planning, that is, a CT image present just before treatment is performed.

The statistical data acquisition unit 450 acquires statistical data corresponding to the set RTP data of the patient and the results of the comparison between two medical images from the statistical model.

For example, as shown in FIG. 5, statistical data corresponding to the results of the comparison between the CT image before planning and the CT image just before treatment and RTP A set based on the CT image before planning is acquired from the statistical model.

The treatment plan generation unit 460 generates new RTP data based on the statistical data acquired by the statistical data acquisition unit 450 and the personalized data of the patient.

For example, as shown in FIG. 5, the treatment plan generation unit 440 acquires statistical data from the statistical model and generates new RTP data, that is, RTP A', using the acquired statistical data and the personalized data of the patient.

As another embodiment, the treatment plan generation unit 460 may generate new RTP data using a treatment purpose, as well as the statistical data and the personalized data of the patient.

The display unit 470 displays the RTP data generated by the treatment plan generation unit 460 on a screen, thus providing the generated RTP data to the user.

The determination unit 480 may receive user input, that is, input related to whether to use generated RTP data, from the user and determine whether to use the generated RTP data as the RTP data of the patient according to the received user input.

Figure 6:
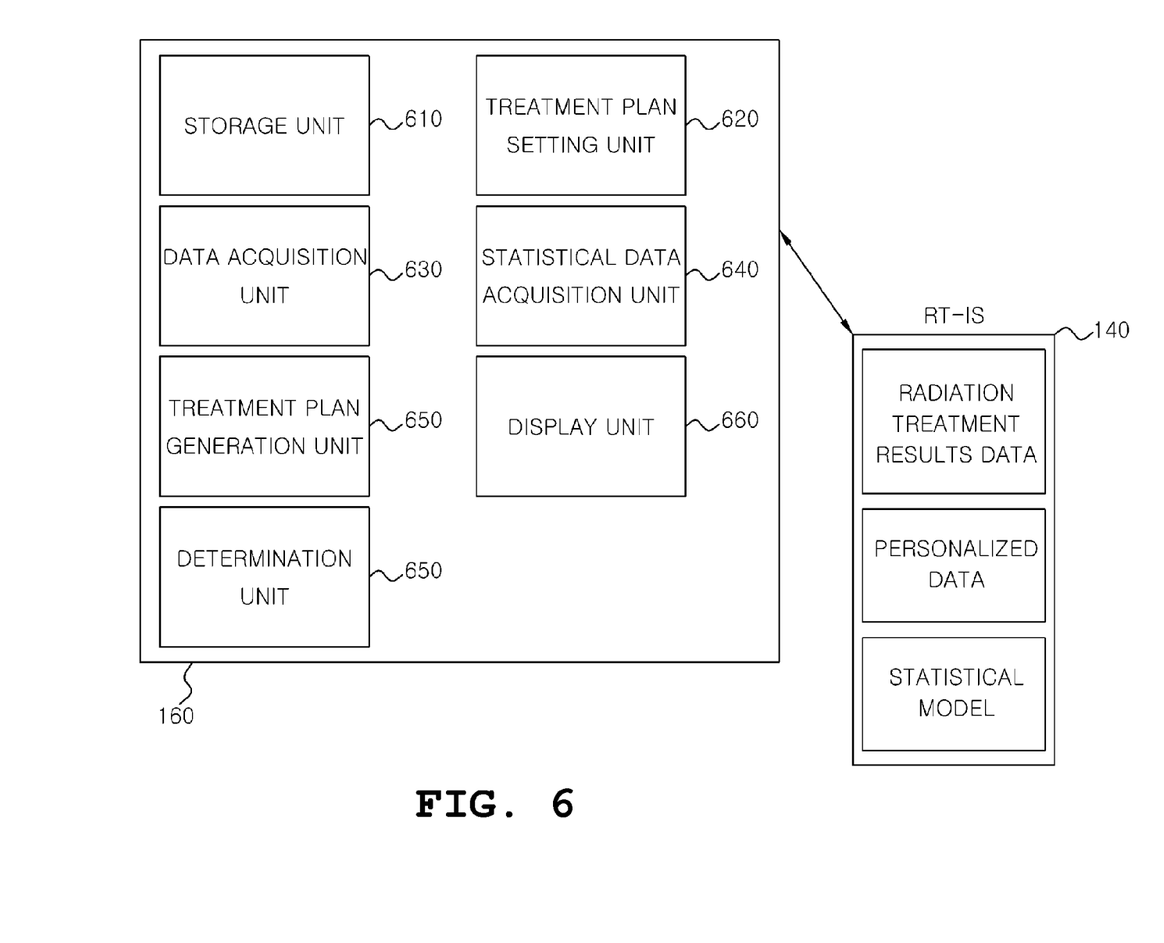
FIG. 6 shows the configuration of an RTP system according to an embodiment of the present invention.

FIG. 6 is a diagram showing the configuration of a radiation treatment planning (RTP) system according to an embodiment of the present invention, and illustrates the configuration of a system for generating RTP data using a statistical model for radiation treatment results data.

Referring to FIG. 6, the RTP system includes a client device 160 and an RT-IS 140 shown in FIG. 1.

The RT-IS 140 stores radiation treatment results data based on the previous RTP data of each patient, the personalized data of the patient, and a statistical model.

In this case, the RT-IS 140 may also store past RTP data of a plurality of patients, radiation treatment results data based on the past RTP data, and medical images of regions of interest of the patients.

Of course, the RT-IS 140 may generate a statistical model for past RTP data, radiation treatment results data based on the past RTP data, and subsequent RTP data based on the radiation treatment results data, and may store the statistical model. Furthermore, the RT-IS 140 may update the statistical model at regular intervals, and may also update the statistical model depending on specific conditions.

The client device 160 includes a storage unit 610, a treatment plan setting unit 620, a data acquisition unit 630, a statistical data acquisition unit 640, a treatment plan generation unit 650, a display unit 660, and a determination unit 670.

The storage unit 610 stores a plurality of RTP data which have been previously modeled, and medical images of a patient as necessary.

Of course, the storage unit 610 may store not only the above-described data, but also relevant data required to establish RTPs in the client device 160 according to the present invention.

The treatment plan setting unit 620 sets RTP data based on a medical image of a region of interest of the patient, that is, the radiation treatment region of the patient, before planning.

In this case, the treatment plan setting unit 620 may set RTP data corresponding to the medical image of the patient among the plurality of RTP data pre-stored in the storage unit 610 and may also set the RTP data in response to user input made by a radiation treatment specialist.

Further, the treatment plan setting unit 620 may set the RTP data by additionally using the personalized data of the patient received from the RT-IS 140.

The data acquisition unit 630 requests and receives radiation treatment results data based on the RTP data, set from the medical image of the patient before planning, and the personalized data of the patient from the RT-IS 140.

The statistical data acquisition unit 640 requests and receives statistical data corresponding to previous RTP data and the radiation treatment results data acquired by the data acquisition unit 630 from the RT-IS 140.

In this case, the RT-IS 140 may acquire statistical data corresponding to the previous RTP data requested by the client device 160 and radiation treatment results data based on the previous RTP data from a previously generated statistical model, and may provide the statistical data to the client device 160.

The treatment plan generation unit 650 generates RTP data in a subsequent fraction for the region of interest of the patient using the statistical data and the personalized data of the patient acquired by the RT-IS 140.

The display unit 660 displays the RTP data generated by the treatment plan generation unit 650 on a screen, thus providing the generated RTP data to the user.

The determination unit 670 may receive user input, that is, input related to whether to use generated RTP data, from the user and determine whether to use the generated RTP data as the RTP data of the patient according to the received user input.

In this way, the RTP apparatus and system according to the present invention establishes new RTP data using statistical data corresponding to RTP data and radiation treatment results data based on the RTP data in a previous fraction, and the personalized data of the patient, thus reducing the time and cost required to establish RTPs.

Further, the present invention may generate new RTP data by additionally considering a radiation treatment purpose, and may generate RTP data in the corresponding fraction using the statistical data corresponding to the results of a comparison between a medical image before planning and a medical image just before treatment and RTP data based on the comparison results within one fraction, thus omitting an existing procedure for establishing RTPs and reducing the time and cost required to generate RTP data.

Figure 7:
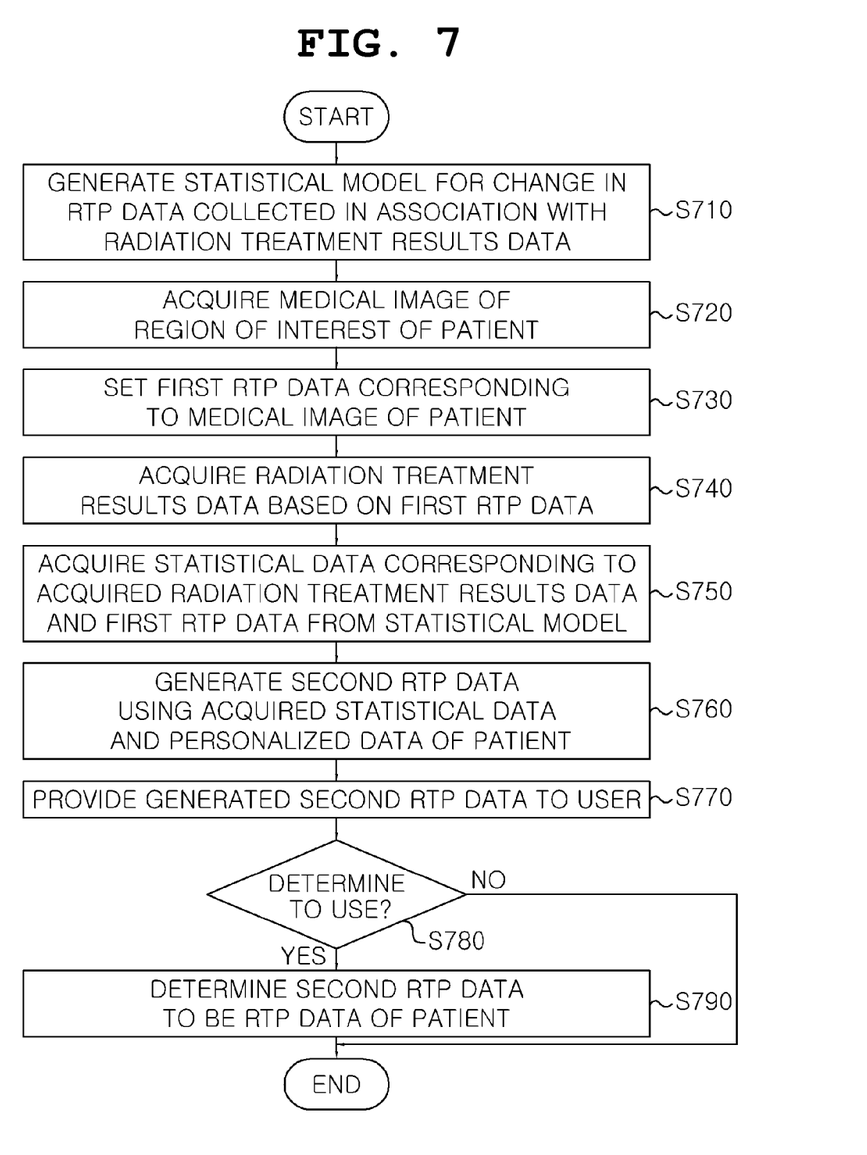
FIG. 7 shows an operation flowchart of an RTP method according to an embodiment of the present invention.

FIG. 7 is an operation flowchart showing an RTP method according to an embodiment of the present invention, and illustrates a process for establishing RTP data using a statistical model related to radiation treatment results data and personalized data.

Referring to FIG. 7, in the RTP method, radiation treatment results data and change data of RTP data based on the radiation treatment results data are collected from a plurality of patients, and a statistical model for a change in the RTP data is generated using the collected data (S710).

In this case, the generated statistical model may include statistical data for respective cases, and the generated statistical model may be stored in an RT-IS or in a client device.

A medical image for a region of interest of a patient in which radiation treatment is to be undergone is acquired, and the first RTP data of the corresponding patient is set using the acquired medical image of the patient (S720 and S730).

Here, the first RTP data of the patient may be set in such a way as to set RTP data corresponding to the medical image of the patient among a plurality of pre-stored RTP data, or may be directly set by a radiation treatment specialist who establishes RTPs. A plurality of pre-stored RTP data may be RTP data modeled in consideration of a treatment purpose, age, a region of treatment, etc., and may also be modeled using RTP data of a plurality of patients.

In this case, at step S730, first RTP data may be acquired using the medical image of the patient and the personalized data of the patient.

If radiation treatment based on the acquired first RTP data is performed and then radiation treatment results data based on the first RTP data is acquired, statistical data corresponding to the acquired radiation treatment results data and the first RTP data is acquired from the statistical model generated at step S710 (S740 and S750).

If the statistical data has been acquired at step S750, new RTP data, that is, second RTP data, is generated using the statistical data and the personalized data of the patient (S760).

If the new second RTP data has been generated, the second RTP data is provided to a user, that is, the radiation treatment specialist, and it is determined whether to use the generated second RTP data as the RTP data of the patient depending on the determination of the user (S770 to S790).

Here, at step S780, if the user determines not to use the generated second RTP data, available RTP data may be provided to the user or, alternatively, a procedure for regenerating new RTP data may be repeated in consideration of the additional input of the user or the like.

In FIG. 7, although a configuration in which the statistical model for the change in the RTP data based on the radiation treatment results data is used has been described, the RTP method according to the present invention is not limited thereto, and, as described above in the apparatus, new RTP data may be generated by additionally using a radiation treatment purpose.

Figure 8:
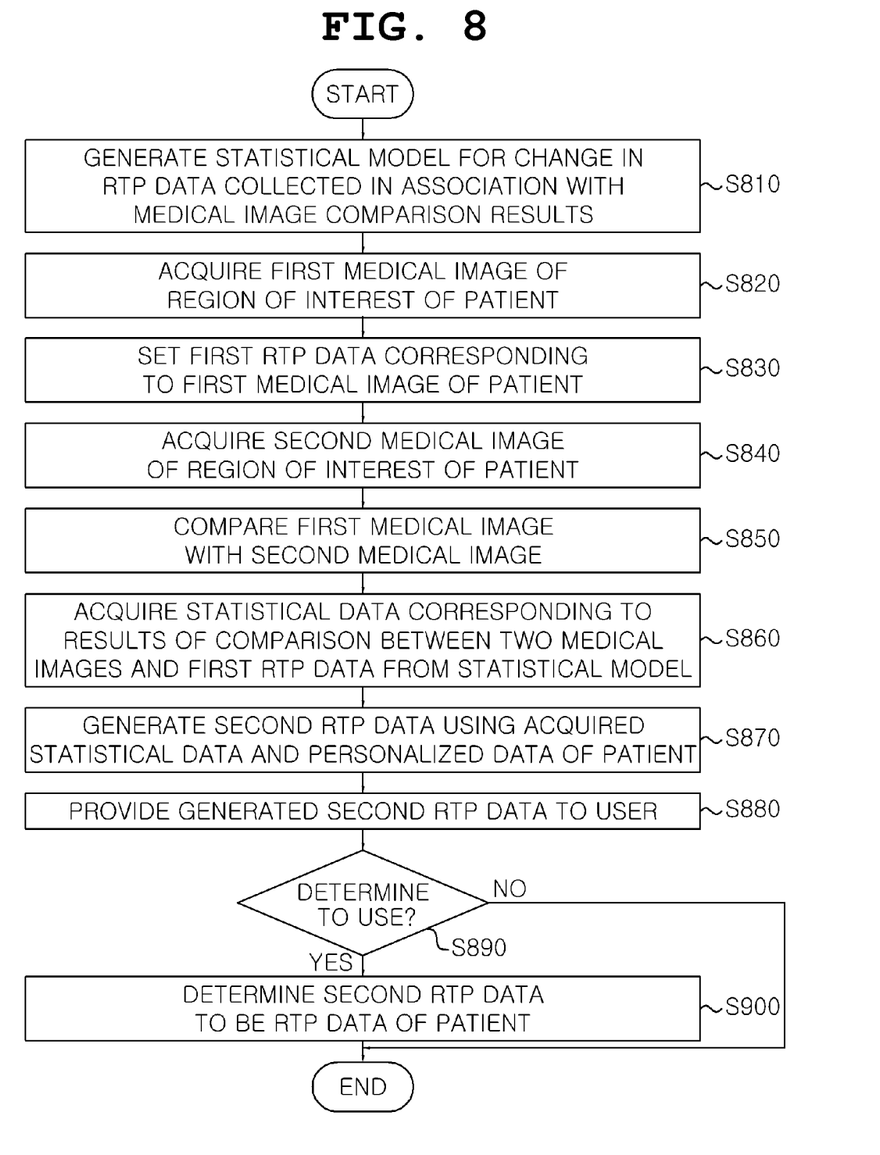
FIG. 8 shows an operation flowchart of an RTP method according to another embodiment of the present invention.

FIG. 8 is an operation flowchart showing an RTP method according to another embodiment of the present invention, and illustrates a process for establishing RTP data using a statistical model for the results of a comparison between two medical images in a single fraction.

Referring to FIG. 8, in the RTP method, the results of the comparison between medical images and the change data of RTP data based on the comparison results are collected from a plurality of patients, and a statistical model for a change in the RTP data is generated using the collected data (S810).

In this case, the generated statistical model may include statistical data for respective cases, and the generated statistical model may be stored in an RT-IS or in a client device.

A medical image of the region of interest of a patient in which radiation treatment is to be undergone is acquired, and the first RTP data of the patient is set using the acquired medical image (S820 and S830).

Here, the first RTP data of the patient may be set in such a way as to set RTP data corresponding to the medical image of the patient among a plurality of pre-stored RTP data, or may be directly set by a radiation treatment specialist who establishes RTPs. A plurality of pre-stored RTP data may be RTP data modeled in consideration of a treatment purpose, age, a region of treatment, etc., and may also be modeled using RTP data of a plurality of patients.

In this case, at step S830, first RTP data may be acquired by additionally using the personalized data of the patient, as well as the medical image of the patient.

If the first RTP data of the patient has been acquired, a second medical image of the patient is acquired before radiation treatment is performed, the acquired first and second medical images of the patient are compared with each other, and statistical data for the results of the comparison between the two medical images is acquired from the statistical model generated at step S810 (S840 to S860).

If the statistical data has been acquired at step S860, new RTP data, that is, second RTP data, is generated using the acquired statistical data and the personalized data of the patient (S870).

If the new second RTP data has been generated, the second RTP data is provided to a user, that is, the radiation treatment specialist, and it is determined whether to use the generated second RTP data as the RTP data of the patient depending on the determination of the user (S880 to S900).

If, at step S890, the user determines not to use the generated second RTP data, available RTP data may be provided to the user or, alternatively, a procedure for regenerating new RTP data may be repeated in consideration of the additional input of the user or the like.

Similar to FIG. 7, although a configuration in which the statistical data and the personalized data are used has been described in FIG. 8, the present invention is not limited thereto, and new RTP data may be generated by additionally using a radiation treatment purpose.

Further, although not shown in FIGS. 7 and 8, in the RTP method of the present invention, the statistical model may be updated at regular intervals, and may also be updated depending on specific conditions.

The radiation treatment planning method according to the embodiment of the present invention may be implemented in the form of program instructions that can be executed via various computer means, and may be stored in a computer-readable medium. The computer-readable medium may include one of program instructions, data files, and data structures or program instructions, data files, and data structures in combination. The program instructions recorded in the computer-readable medium may be program instructions that are specially designed and configured for the present invention or that are well known to and can be used by those having ordinary knowledge in the field of computer software. Examples of the computer-readable medium includes magnetic media such as a hard disk, a floppy disk and magnetic tape, optical media such as CD-ROM and a DVD, magneto-optical media such as a floptical disk, and hardware devices that are specially configured to store and execute program instructions, such as ROM, RAM, and flash memory. The examples of the program instructions include not only machine language code that is generated by a complier, but also high-level language that can be executed by a computer. The above-described hardware apparatus may be configured to operate as one or more software modules in order to perform the operation of the present invention, and vice versa.

According to the present invention, new RTPs for a plurality of patients are generated using statistical models for the change histories of past RTP data of the patients and the personalized data of the individual patients, thus establishing RTP data considering the personal characteristics of respective patients and reducing the time and cost required to establish RTPs.

In detail, the present invention can obtain the corresponding statistical data from a statistical model previously generated in association with radiation treatment results data using previous RTP data of each patient and radiation treatment results data (including historical information such as dose volume histogram (DVH) and radiation doses) based on the previous RTP data, or a statistical model previously generated in association with medical image comparison results using the results of a comparison between two medical images of the patient and preset RTP data of the patient, and generates subsequent RTP data in consideration of the acquired statistical data and the personalized data of the patient (including personal information about the patient, medical history of the patient, etc.), thus reducing the time required to generate RTP data and effectively establishing subsequent RTP data in conformity with the personal characteristics of the patient.

Furthermore, the present invention can generate new RTP data by additionally considering a radiation treatment purpose, and so a medical imaging procedure and an existing RTP establishment procedure can be omitted by means of the new RTP data, thus reducing the time and cost required to generate RTP data.

Although the present invention has been described with reference to specific contents, such as detailed components, the above description is intended merely to help the overall understanding of the present invention, the present invention is not limited to the above embodiments, and those having ordinary knowledge in the technical field to which the present invention pertains can perform variations and modifications in various manners from the above description.

Accordingly, the spirit of the present invention should not be limited to the above-described embodiments, and the accompanying claims and equal or equivalent modifications thereof should be interpreted as falling within the range of the spirit and scope of the present invention.

What is claimed is:

1. A radiation treatment planning apparatus comprising:
   a processor configured to:
   generate a statistical model for a change in radiation therapy plan (RTP) data based on change data of RTP data collected in association with radiation therapy results data, wherein the change data of RTP data is based on a difference between a first previous RTP data before a previous radiation therapy at least associated with the radiation therapy results has been executed and a second previous RTP data after the previous radiation therapy has been executed, wherein the difference depends at least on a radiation therapy result resulted from the first previous RTP data;
   set first RTP data based on a medical image of a region of interest of a patient;
   acquire first radiation therapy results data resulting from the first RTP data;
   acquire statistical data corresponding to the first RTP data and the first radiation therapy results data from the statistical model;
   generate second RTP data using the statistical data and personalized data of the patient; and
   acquire second radiation therapy results data resulting from the second RTP data.

2. The radiation treatment planning apparatus of claim 1, wherein the personalized data includes at least one of age, gender, weight, height, medical history, occurrence of menopause, diagnosis, medical history, an Eastern Cooperative Oncology Group (ECOG)/Karnofsky Performance Status (KPS) index, regional lymph Node, distant Metastasis (TNM) class, chemical therapy, a region of treatment, a treatment pattern, immunity, sensitivity, and singularities of past treatment.

3. The radiation treatment planning apparatus of claim 1, wherein the processor is further configured to:
   generate the second RTP data using the statistical data and a treatment purpose of RTP data to be generated.

4. The radiation treatment planning apparatus of claim 1, wherein the processor is further configured to:
   set the first RTP data corresponding to the medical image among a plurality of preset RTP data.

5. The radiation treatment planning apparatus of claim 4, wherein the processor is further configured to:
   set the first RTP data among the plurality of RTP data using the medical image and personalized data of the patient.

6. The radiation treatment planning apparatus of claim 1, wherein the processor is further configured to:
   provide the second RTP data to a user, and determining whether to use the second RTP data as RTP data of the patient depending on input of the user.

7. A radiation treatment planning apparatus comprising:
   a processor configured to:
   generate a statistical model for a change in radiation therapy plan (RTP) data based on change data of RTP data collected in association with results of a comparison between medical images, wherein the change data of RTP data is based on a difference between a first previous RTP data based on a first previous medical image acquired before planning the first previous RTP data and a second previous RTP data based on a second previous medical image acquired after planning the first previous RTP data, wherein the difference between the first previous RTP data and the second previous RTP data depends at least on a difference between the first previous medical image and the second previous medical image;

set first RTP data based on a first medical image of a region of interest of a patient;

compare a second medical image acquired from the region of interest with the first medical image;

acquire statistical data corresponding to the results of the comparison between the first medical image and the second medical image and the first RTP data from the statistical model; and generate second RTP data using the statistical data and the personalized data of the patient.

8. The radiation treatment planning apparatus of claim 7, wherein the personalized data includes at least one of age, gender, weight, height, medical history, occurrence of menopause, diagnosis, an Eastern Cooperative Oncology Group (ECOG)/Karnofsky Performance Status (KPS) index, regional lymph Node, distant Metastasis (TNM) class, chemical therapy, a region of treatment, a treatment pattern, immunity, sensitivity, and singularities of past treatment.

9. The radiation treatment planning apparatus of claim 7, wherein the processor is further configured to:
generate the second RTP data using the statistical data and a treatment purpose of RTP data to be generated.

10. A radiation treatment planning method comprising:
generating, by a processor, a statistical model for a change in radiation therapy plan (RTP) data based on change data of RTP data collected in association with radiation treatment results data, wherein the change data of RTP data is based on a difference between a first previous RTP data before a previous radiation therapy at least associated with the radiation therapy results has been executed and a second previous RTP data after the previous radiation therapy has been executed, wherein the difference depends at least on a radiation therapy result resulted from the first previous RTP data;
setting, by the processor, first RTP data based on a medical image of a region of interest of a patient;
acquiring, by the processor, first radiation therapy results data resulting from the first RTP data;
acquiring, by the processor, statistical data corresponding to the first RTP data and the first radiation therapy results data from the statistical model;
generating, by the processor, second RTP data using the statistical data and personalized data of the patient; and
acquiring, by the processor, second radiation therapy results data resulting from the second RTP data.

11. The radiation treatment planning method of claim 10, wherein the generating the second RTP data is configured to generate the second RTP data using the statistical data and a treatment purpose of RTP data to be generated.

12. The radiation treatment planning method of claim 10, further comprising providing, by the processor, the second RTP data to a user, and
determining, by the processor, whether to use the second RTP data as RTP data of the patient depending on input of the user.

13. A radiation treatment planning method comprising:
generating, by a processor, a statistical model for a change in radiation therapy plan (RTP) data based on change data of RTP data collected in association with results of a comparison between medical images, wherein the change data of RTP data is based on a difference between a first previous RTP data based on a first previous medical image acquired before planning the first previous RTP data and a second previous RTP data based on a second previous medical image acquired after planning the first previous RTP data, wherein the difference between the first previous RTP data and the second previous RTP data depends at least on a difference between the first previous medical image and the second previous medical image;
setting, by the processor, first RTP data based on a first medical image of a region of interest of a patient;
comparing, by the processor, a second medical image acquired from the region of interest with the first medical image;
acquiring, by the processor, statistical data corresponding to the results of the comparison between the first medical image and the second medical image and the first RTP data from the statistical model; and
generating, by the processor, second RTP data using the statistical data and the personalized data of the patient.

* * * * *